United States Patent [19]

Wells

[11] 4,436,634
[45] Mar. 13, 1984

[54] METHOD AND APPARATUS FOR SEPARATING CELLS BY SEDIMENTATION VELOCITY

[75] Inventor: John R. Wells, Los Angeles County, Calif.

[73] Assignee: Wescor, Inc., Logan, Utah

[21] Appl. No.: 249,816

[22] Filed: Apr. 1, 1981

[51] Int. Cl.$^3$ .............................................. B01D 21/24
[52] U.S. Cl. ................................... 210/800; 210/241; 210/519
[58] Field of Search ................. 210/800, 801, 927, 94, 210/513–519, 247, 248, 319, 241, 532.2

[56] References Cited

U.S. PATENT DOCUMENTS

| | | | |
|---|---|---|---|
| 3,556,502 | 1/1971 | Rheinlander et al. | 210/800 X |
| 3,681,562 | 8/1972 | Winzen | 210/94 |
| 3,709,361 | 1/1973 | Miller | 210/94 X |
| 4,253,964 | 3/1981 | Pielkenrood | 210/513 |

OTHER PUBLICATIONS

"Separation of Bone Marrow Cells by Sedimentation at Unit Gravity," *Nature*, vol. 214, pp. 824–825, May, 1967.
Edwards et al., "Differentation of Rosette-Forming Cells, etc.", *Journal of Immunology*, vol. 105, 9/1970, pp. 719–729.
Brochure on LACS Cell Separator.

Primary Examiner—Thomas G. Wyse
Attorney, Agent, or Firm—Mallinckrodt & Mallinckrodt

[57] ABSTRACT

A method and apparatus for separating cells according to differences in sedimentation velocity comprises a vessel preferably constructed from a cylindrical body of ring formation, the height of which is substantially less than its diameter, and from top and bottom plates sealingly and removably attached to the ring. The vessel is preferably mounted on a tiltable platform for controlled movement between tilted and horizontal positions and has a small horizontal cross-sectional area in the tilted position relative to such area in the horizontal position. The vessel is provided with two ports; a lower port communicating with a lowermost level of the vessel while in the tilted position and an upper port communicating with the uppermost level in the tilted position. Flow distributing structure is provided preferably between each port and the interior of the vessel whereby the force of liquid flowing into the vessel through a port is dissipated. A gradient liquid and a cell suspension are loaded into the vessel while it is in a tilted position. Thereafter, the vessel is rotated to the horizontal position for cell separation. After separation, the vessel is reoriented to the tilted position, and the gradient liquid containing separated cells is collected as various fractions.

16 Claims, 12 Drawing Figures

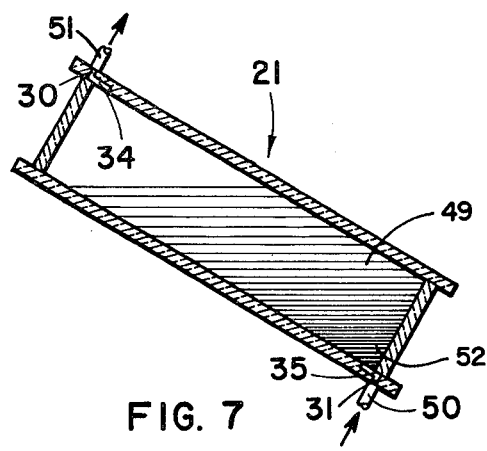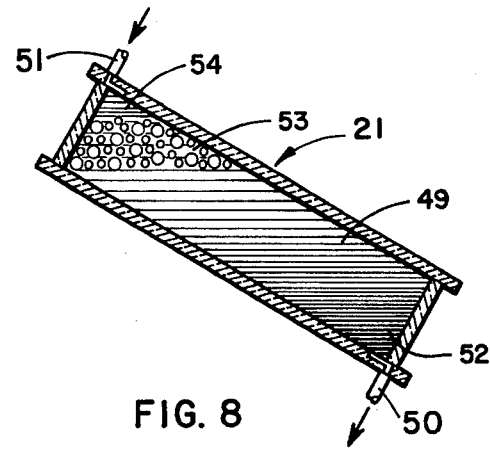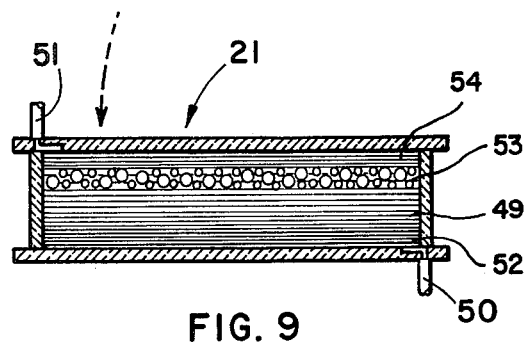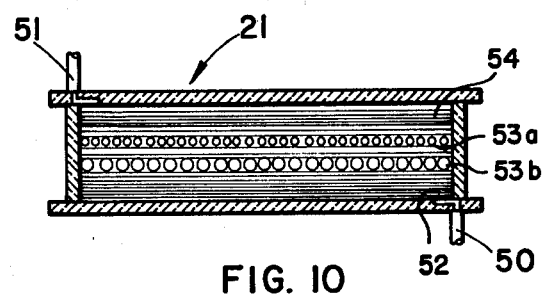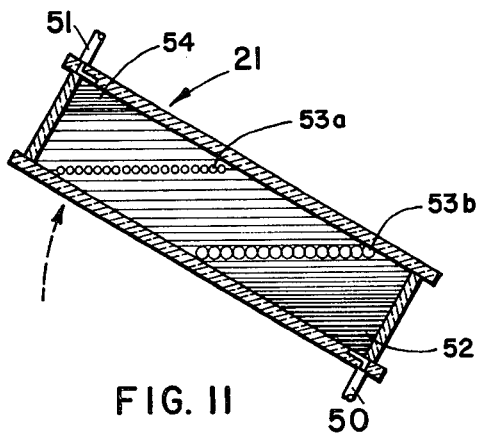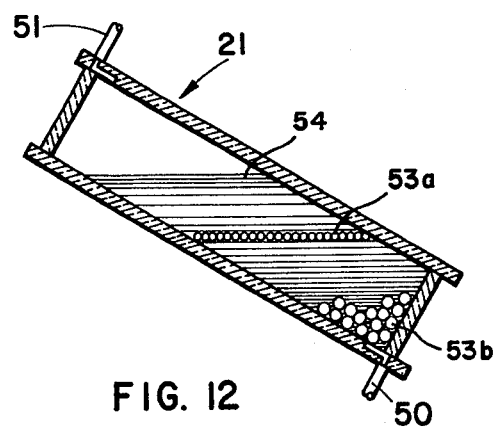

METHOD AND APPARATUS FOR SEPARATING CELLS BY SEDIMENTATION VELOCITY

BACKGROUND OF THE INVENTION

1. Field

The invention relates to methods and apparatus for separating cells having differing sedimentation velocities.

2. State of the Art

The term "sedimentation velocity" refers to the rate at which a particle suspended in a liquid will fall due to gravity or other force applied. A particle, such as a cell, will fall at a rate which is dependent upon the strength of the gravitational force; the size, shape, and density of the particle; and the density and viscosity of the liquid in which the particle is suspended.

Differences in the sedimentation velocities of dissimilar particles may be used to separate the various particles from one another.

The gravitational force, the density of the supporting liquid, and the viscosity of the supporting liquid will be constant with respect to all particles which are loaded onto the supporting liquid in the separator apparatus. Thus, the only variables are the size, shape, and density of the individual particles. When the particles to be separated are cells, the number of variables decreases still further since cells are essentially spherical in shape and the densities of various cells are usually similar. Thus, the sedimentation velocity of a cell is a function of the size of the cell; the larger the cell, the higher its sedimentation velocity.

In the past, cells hve been separated by filling a chamber with a gradient of Ficoll (trademark of Pharmacia Fine Chemicals of Piscatuay, N.J., for a polysucrose material) or other solution such as sucrose or a large molecular weight polymer or protein. One device used to separate cells consists of a rectangular vessel having a height significantly greater than either dimension of its base. The gradient liquid is added to this vessel by means of a tube lowered into the top of the vessel, and the tube is raised by means of a float as the gradient is introduced so that gradient is always introduced at the top surface of liquid in the vessel. After introduction of the gradient, the cell suspension is loaded and the top sealed off. During gradient introduction and cell loading, both the gradient and cell suspension are passed through a sieve to minimize mixing. Then the vessel is rotated 90° so that the thickness of isodense layers of liquid and the thickness of the layer of cells substantially decrease. After the cells have been given time to separate due to their differences in sedimentation velocity, the vessel is returned to its original position, a tube that is attached to an inverted funnel is lowered into the vessel, and the gradient is drawn off from the top and collected as various fractions.

Another device used to separate cells by sedimentation velocity is disclosed in U.S. Pat. No. 3,709,361. This device employs a cylindrical sedimentation vessel mounted for rotation between a horizontal position and a tilted position and has inlet/outlet ports located in the cylinder portion adjacent to the flat top and bottom walls. These ports extend from the cylinder portion at an obtuse angle to the top and bottom walls, respectively, in order to reduce the amount of mixing of isodense layers of liquid contained in the sedimentation vessel.

SUMMARY OF THE INVENTION

According to the invention, a mixture of particles having different sedimentation velocities may be quickly and easily separated, even though inlet/outlet ports are located in the flat top and bottom walls of a cylindrical sedimentation vessel contrary to the teachings of the aforementioned U.S. Pat. No. 3,709,361, but substantially corresponding in other respects thereto.

As in such patent, a cell separation vessel adapted to be moved between a tilted position and a horizontal position at different stages of the cell separation process is preferably though not necessarily utilized. Initially, the vessel is oriented to a tilted position so that it presents a relatively small horizontal cross-sectional area with respect to the horizontal cross-sectional area when in the horizontal position. The vessel is completely filled with a usual gradient liquid, followed by a usual cushioning liquid introduced through a port located at the lowermost level of such vessel when it is in the tilted position, after which a usual cell suspension containing cells to be separated, followed by a usual overlay liquid, are introduced through a corresponding port located at the uppermost level of the vessel, as a corresponding quantity of the gradient liquid is withdrawn through the lower port. When in the tilted position, the vessel forms what is in effect a funnel in the area surrounding each of the two ports. This means that the depth of the isodense layers of the gradient liquid will be substantially increased in the vicinity of the ports, and, together with the relatively small horizontal cross-sectional area of the vessel in the tilted position, mixing of such isodense layers is reduced over what would occur otherwise. Also premature sedimentation of the cells is largely avoided.

In accordance with the invention, when the inlet/outlet ports are located in the flat top and bottom walls of the vessel with their openings into the interior of the vessel offset from the interior of the vessel, contrary to the teachings of said U.S. Pat. No. 3,709,361, they are provided with respective liquid-flow-distributing structure, which includes a baffle or an expansion chamber or both to divert the direction of flow of incoming liquid and to spread or fan out the transverse cross-sectional area of flow in order to significantly reduce the velocity of flow and minimize the chance that the isodense layers will mix during filling and loading of the vessel.

The presently preferred embodiment of the separation vessel comprises a cylindrical body member in the form of a transparent ring having a height substantially less than its diameter and incorporating both baffles and expansion chambers for diverting flow of incoming liquid. Circular top and bottom plates larger in diameter than the body member are secured in place by means of a circumferential series of bolts externally of the ring, and O-rings serve to seal the interfaces between the ring and the top and bottom plates, respectively. The separation vessel as so constructed is mounted on a tilting platform, where it is initially oriented at an angle between 10° and 80° with respect to the horizontal so the superficial areas of the respective isodense layers will be relatively small. A port passes through the bottom plate within the area of the junction of the bottom plate and the ring at the lowermost point assumed by the vessel in the tilted position, so as to open onto the lower end face of the ring which serves as a baffle for diverting flow of the incoming liquid. Another port similarly passes through the top plate at the uppermost point assumed by the vessel in the tilted position, so as to open onto the upper end face of the ring which serves as a baffle for diverting flow of the incoming liquid. Relatively shallow expansion chambers extend from the port openings toward the interior of the vessel to spread or fan out the diverted incoming flows of liquid, thereby significantly decreasing the velocities thereof. Incoming liquid is normally pumped through a relatively narrow tube at a rate which could cause undesirable mixing of the isodense layers. However, as previously indicated, the shape of the vessel causes the isodense layers to be thicker in the vicinity of the ports, thus decreasing problems of mixing. Additionally, and in accordance with the invention the liquid-flow-distributing structure provided by the baffle and expansion chamber at the interface between each port and interior of the vessel significantly decreases the velocity of the incoming flow and directs it into the vessel with a minimum of disturbance to the liquid therein.

The baffles and expansion chambers could be provided in either the inner faces of the top and bottom plates or the end faces of the cylindrical body member. Again, they could be either localized in extent relatively to the respective ports or could be of unlimited extent circumferentially of the vessel, as would be the case if an annular ledge along the inner margin of an end face of the cylindrical body and in communication with the corresponding port were provided instead of a localized chamber at the location of the port.

Although a tiltable separation vessel is preferred for the reasons indicated, the flow distributing structure of the invention could be used with a stationary separation vessel as will be apparent to those skilled in the art.

THE DRAWINGS

In the accompanying drawings, which represent the best mode presently contemplated for carrying out the invention:

FIG. 1 is a perspective view of the apparatus of the invention with the separation vessel tilted into the initial loading position;

FIG. 2, a top plan view of the separation vessel rotated 90° from its position in FIG. 1, part of the top plate being broken away to reveal otherwise hidden parts;

FIG. 3, a vertical section taken on the line 3—3 of FIG. 2;

FIG. 4, a fragmentary vertical section taken on the line 4—4 of FIG. 2 and drawn to a larger scale;

FIG. 5, a fragmentary vertical section taken on the line 5—5 of FIG. 2 and drawn to the larger scale of FIG. 4;

FIG. 6, a circuit diagram of the electrical system powering the motor for rotating the separation vessel between its two working positions shown schematically in FIGS. 7-12;

FIG. 7, a schematic representation of the separation vessel as a cushion liquid is being introduced following introduction of a gradient liquid;

FIG. 8, a similar schematic representation of the separation vessel as an overlay liquid is being introduced following loading of cells;

FIG. 9, a schematic representation of the separation vessel immediately following rotation to the horizontal position, showing the condition before cell separation;

FIG. 10, a similar schematic representation showing the condition after cell separation;

FIG. 11, a schematic representation showing the separation vessel reoriented to the tilted position following cell separation; and FIG. 12, a similar schematic representation showing isodense layers being withdrawn from the separation vessel.

DETAILED DESCRIPTION OF THE ILLUSTRATED EMBODIMENT

Figure 1:
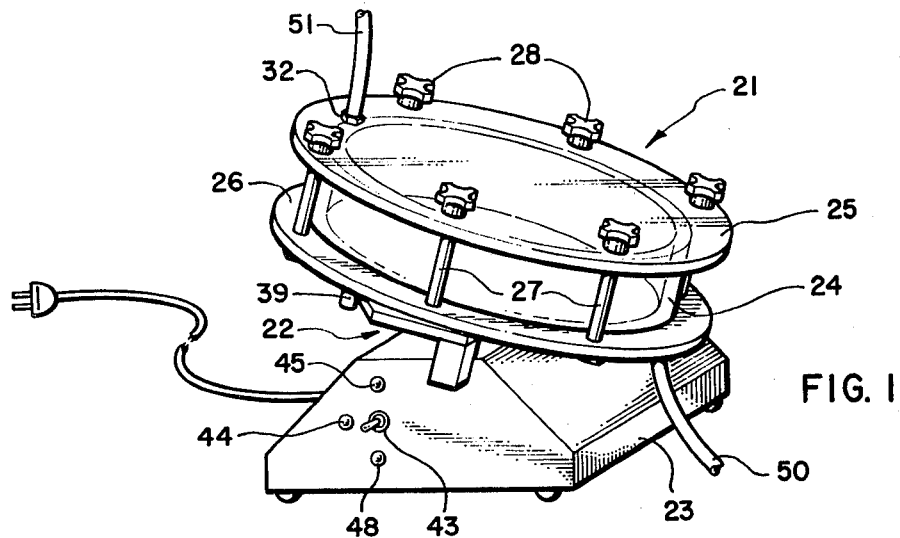

In its illustrated form, FIG. 1, the cell separation apparatus of the invention comprises a separation vessel 21 resting on a platform 22, which is movable between a tilted and a horizontal position by means of mechanism including an electric motor (not shown) housed in a box-like base structure 23. The shape of the vessel is such that its horizontal cross-sectional area in the tilted position is significantly less than the horizontal cross-sectional area in the non-tilted position.

Vessel 21 is made up of a ring 24 forming a cylindrical body having, as illustrated, an open and unobstructed interior, a circular top plate 25, and a corresponding bottom plate 26, both of greater diameter than the ring. The top and bottom plates 25 and 26 are attached to the ring by means of a circumferential series of bolts 27, which pass through the bottom and top plates outside of ring 24 and onto which knobs 28 are screwed for tightly securing the assembly together. O-rings 29, FIGS. 2-5, form seals between ring 24 and the top and bottom plates 25 and 26, respectively. The ring 24 has a height substantially less than its diameter. Ring 24 and plates 25 and 26 are preferably machined from a transparent plastic material.

Figure 2:
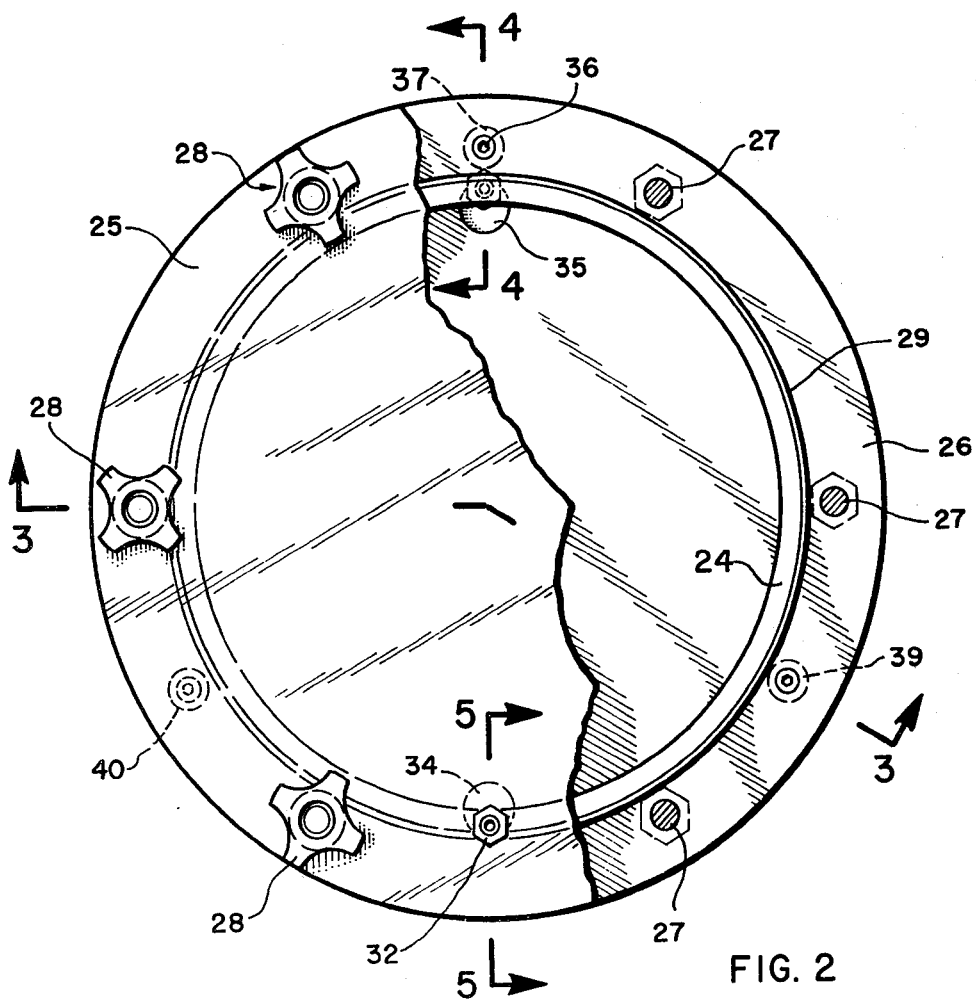
Figure 3:
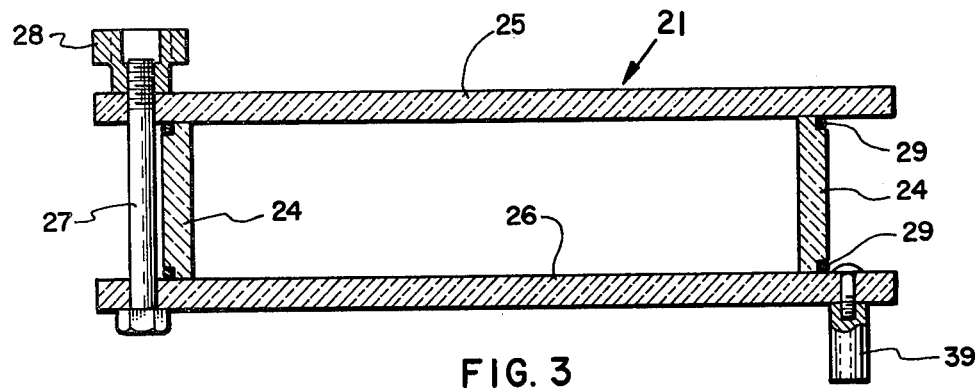
Figure 4:
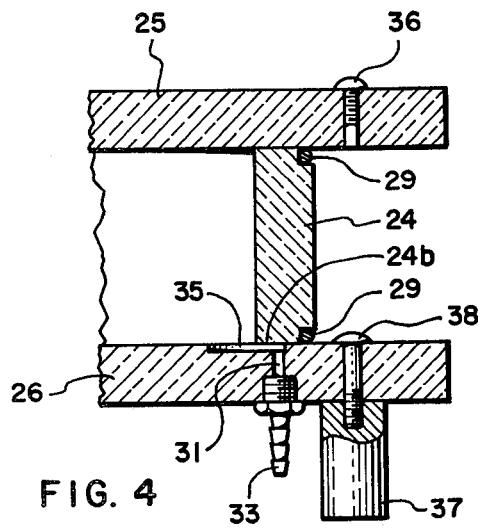
Figure 5:
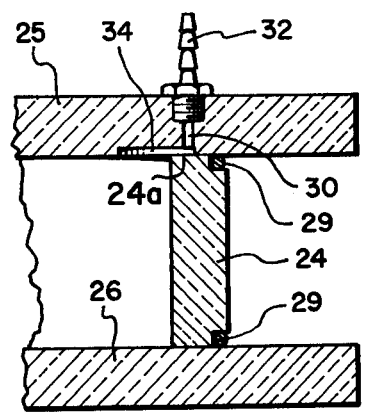

An upper port 30, FIG. 5, and a lower port 31, FIG. 4, equipped with tube-connection fittings 32 and 33, respectively, are provided in top plate 25 and bottom plate 26, respectively, to allow for filling and removal of liquid. Shallow expansion chambers 34 and 35, which are preferably circular as shown in FIG. 2 and which are considerably broader than the diameter of the respective ports, are formed in the top and bottom plates, respectively, such that ports 30 and 31 communicate with respective portions of the expansion chambers 34 and 35 farthest from the axis of ring 24 and that their openings into the interior of the vessel 21 are offset from the interior of such vessel. Expansion chambers 34 and 35 are preferably located so that approximately one-half of the area thereof rests above and beneath the upper and lower ends, respectively, of ring 24, as illustrated in FIGS. 5 and 4. This arrangement causes incoming liquid to from ports 30 and 31 impact upon upper and lower end faces 24a and 24b, respectively, of the ring 24, serving as a baffles, and to be diverted into the corresponding expansion chamber.

Port 30 is located at the uppermost point of the separation vessel 21 when in the tilted position of FIGS. 1, 7, 8, 11, and 12. Port 31 is similarly located at the lowermost point. It should be understood that if a vessel were used having a different shape, it would be possible to have an uppermost level and lowermost level rather than merely a single uppermost point and lowermost point while in the tilted position.

In order to assure that vessel 21 is assembled correctly after it has been taken apart for cleaning, a screw 36, FIGS. 2 and 4, is fitted into top plate 25 directly over a leg 37, which is held in place in bottom plate 26 by a screw 28. These may all be color-coded for convenience. Two other legs 39 and 40, FIG. 2, also extend from bottom plate 26 so that the vessel 21 may be placed on a flat surface without resting on bottom fitting 33.

For use, vessel 21 is placed on the platform 22. It is positioned correctly on the platform by means of the legs 39 and 40, which fit snugly against the edge of platform 22. The heads of two of the bolts 27 are accommodated by holes (not shown) cut into the platform 22. This combination prevents the vessel 21 from sliding off platform 22 when in the tilted position.

Figure 6:
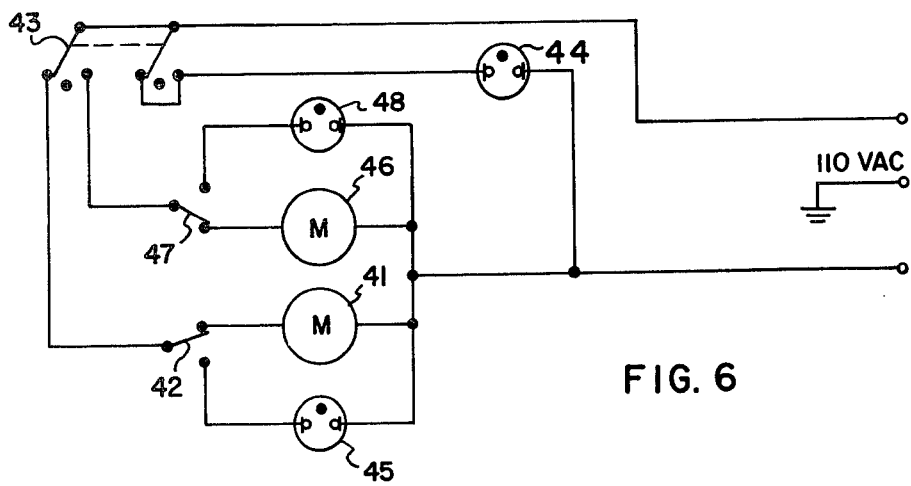

A suitable electrical system for controlling movement of vessel 21 from the horizontal FIGS. 9 and 10, to the tilted position, FIGS. 7, 8, 11, and 12, and vice versa is shown in the circuit diagram of FIG. 6. When 110 volts AC is applied to the circuit as shown, current flows through motor 41, single-pole double-throw limit switch 42, and double-pole double-throw center-off switch 43. Current also flows through power indicator lamp 44. The motor 41 is of a one-half sinusoidal type such that initial movement of the platform 22 is very slow. The rate of movement accelerates until mid-point, at which time it begins to decelerate. This allows the vessel 21 to be moved from the horizontal to the tilted position without mixing of isodense layers of liquid contained therein. When platform 22 has rotated vessel 21 to a selected angle between about 10° and 80° with respect to the horizontal, limit switch 42 is mechanically thrown to its other position, thus causing current to flow through indicator lamp 45 and to cease flowing through motor 41. The platform 22 is raised to an angle of about 30° in current prototypes. An appropriate motor may require between 3-5 minutes to effect this rotation. It should be realized that a single one-half sinusoidal motor that is reversible could be used with appropriate changes in the electrical wiring readily apparent to those skilled in the art.

Switch 43 may be placed in the center-off position when the platform 22 is in the desired positon.

When it is desired to lower platform 22 to the horizontal, switch 43 is put in its other position so that current flows through motor 46 and power indicator lamp 44. Motor 46 is also one-half sinusoidal type. As the platform 22 begins to lower, limit switch 42 returns to its original position. When platform 22 reaches the horizontal, limit switch 47 is mechanically thrown to its other position thus halting flow of current to motor 46 and passing current through indicator lamp 48. Again, switch 43 may be placed in the center-off position when the platform 22 is in the desired position. Also, limit switch 47 will return to its original position when platform 22 is once more raised from the horizontal.

FIG. 1 shows switch 43 and indicator lamps 44, 45 and 48. As discussed previously in connection with FIG. 6, the center position of switch 43 does not apply power to any circuit component. Raising the switch 43 to the upper position causes lamp 44 to light and causes platform 22 to rotate from the horizontal position. When the platform reaches an angle of approximately 30°, lamp 45 lights to indicate that fact. Moving switch 43 to the lower position causes lamp 44 to light and causes platform 22 to rotate to the horizontal. When platform 22 reaches the horizontal, lamp 48 will light.

The cell separation steps are shown schematically in FIGS. 7-12. As shown in FIG. 7, the vessel 21 is initially tilted to an angle between about 10° and 80° with respect to the horizontal, e.g. 30°. An angle of 45° will give the maximum effect. A gradient liquid 49, such as 2-4% (w/w) Ficoll, is introduced through port 21 by means of a tube 50 attached to fitting 33, FIG. 4. Air is simultaneously forced out through port 30 into tube 51 attached to fitting 32, FIG. 5. Liquid flowing through port 31 strikes the bottom end surface 24a, FIG. 4, of ring 24, which serves as a baffle and diverts the liquid 90° as it flows into expansion chamber 35 before reaching the main body of liquid in the vessel. The abrupt change of direction evens out and diminishes the force of incoming liquid and thus considerably reduces the tendency toward mixing of the isodense layers.

The diameter of expansion chamber 35 is considerably larger than that of port 31, so that, along with the depth of such chamber, the incoming liquid will fan out as it leaves the port, thus significantly diminishing the velocity of the incoming liquid. It has been found that a circular expansion chamber having a depth of about 0.020 inches is satisfactory when used in conjunction with a baffle diverting liquid flow by 90°.

This flow distributing structure, here comprising the combination of flow diverting baffle and expansion chamber, minimizes mixing of isodense layers of gradient liquid. However, it should be realized that the use of baffles or expansion chambers alone as the flow distributing structure under suitable circumstances can effectively reduce the flow velocity of incoming liquid. If the ports are directed into the respective expansion chambers at angles of 180° or thereabouts, such chambers should have larger areas than otherwise. Whether baffles or expansion chambers alone or the two in combination are utilized, it should be realized that they are placed relative to the ports in respective locations between the respective ports and the interior of the vessel, i.e. away and protected from the main body of liquid in the vessel. Use of the baffle substantially equalizes the velocity of flow throughout the cross-sections of the stream of inflowing liquid.

It should be understood that, although the preferred embodiment places the expansion chambers 34 and 35 in the top and bottom plates respectively, it would also be possible to have the expansion chambers formed in the respective end faces of the ring. However, this would be disadvantageous in instances such as that illustrated in which the ports are formed through the end plate, since it would require a particular alignment of the end plates with the ring which is unnecessary with the illustrated preferred embodiment.

After the gradient liquid 49 has been introduced into the vessel 21, a relatively dense cushion material 52 is similarly introduced through lower port 31 while some of the gradient liquid passes out through upper port 30. Next, a cell suspension 53, FIG. 8, is loaded through upper port 30 while some of the cushion material 52 flows out of lower port 31. (The cells of cell suspension 53 are drawn to an exaggerated scale in FIGS. 7-12 for convenience of illustration). Finally, an overlay material 54 is added onto the cell suspension in the same manner. All of these liquids are of the types usual in this art.

In a vessel 21 having an internal capacity of 1000 milliliters, approximately 25-70 mls of cell suspension may be added. The concentration of the cells must be low enough to avoid streaming. In the case of mammalian cells, a concentration of about $1 \times 10^6$ cells/ml has been found satisfactory. It is important that sample loading be completed as rapidly as possible so that separation does not begin while cells are still being loaded. Yet, it is important to avoid excessive turbulence which will result in mixing of the isodense layers of liquid. A loading time of approximately three minutes is a reasonable compromise. Such rapid loading time would not be possible in the absence of the liquid flow distributing structure of the invention.

After the various liquids have been introduced into the vessel 21, the ports are sealed, as by using a hose clamp on tubes 50 and 51 and the vessel is rotated to the horizontal position shown in FIG. 9. The horizontal cross-sectional area of the vessel 21 while in the horizontal position is substantially larger than the horizontal cross-sectional area in the tilted position. Thus, the isodense layers will spread out to fill the larger area, and will correspondingly decrease in thickness. This is shown schematically in FIGS. 8 and 9. The walls of the vessel are preferably vertical when in the horizontal position so that sedimenting cells can sediment without obstruction. The overlay 54 is used to separate the cells 53 from the top plate 25 of the vessel 21, so they will not cling to it. Such overlay also insures that the thickness of the cell suspension 53 is constant. The volume and concentration of cells in the cell suspension 53 is such that there is substantially a single layer of cells when the vessel 21 is initially moved to the horizontal position. The cushioning is similarly used to aid in evening out the lowest isodense layers in the gradient.

The vessel is left undisturbed for a period of between about one to four hours while the cells separate according to sedimentation velocity as indicated in FIG. 10, see 53a and 53b. Then, the vessel 21 is reoriented to the tilted position as indicated in FIG. 11. This causes the isodense layers to increase in thickness once more, thus increasing the resolution of isodense layers containing the various cell fractions and also decreasing the possibility of mixing the isodense layers as the vessel 21 is emptied. The vessel is emptied through port 31, and the various fractions containing separated cells are collected.

Although it is preferred to provide flow distributing structure in association with both the lower and the upper ports in any separation vessel incorporating the invention, so that loading of the cell suspension can take place through the upper port after the vessel has been filled with a gradient liquid, the upper port could be merely a vent through which air and excess liquid would escape and the cell suspension could be loaded through the bottom port before introducing the gradient liquid. In such case, it would be unnecessary to provide flow distributing structure in association with the upper port.

Whereas the invention is here illustrated and described with specific reference to an embodiment thereof presently contemplated as the best mode of carrying out such an invention in actual practice, it is to be understood that various changes may be made in adapting the invention to different embodiments without departing from the broader inventive concepts disclosed herein and comprehended by the claims that follow.

I claim:

1. Apparatus for separating cells of differing sedimentation velocities, comprising a closed separation vessel having an open and unobstructed interior and adapted to be mounted for tilting from and back to horizontal position; a relatively very small lower port located at the lowermost level of the interior of said vessel when said vessel is in its tilted position; a similar upper port located at the uppermost level of the interior of said vessel when said vessel is in its tilted position, the opening of at least the lower port into the interior of the vessel being offset from the interior of the vessel; and flow distributing means having flow distributing structure located between the lower port and the interior of the vessel and offset from the interior of the vessel for fanning out and decreasing the velocity of the incoming flow and thereby reducing the tendency of incoming liquid to disturb isodense layers of liquid contained in the vessel.

2. Apparatus according to claim 1, wherein the flow distributing structure comprises a baffle against which the flow from the port is directed for expansion and velocity reduction before it enters the interior of the vessel.

3. Apparatus according to claim 1, wherein the flow distributing structure comprises a shallow expansion chamber leading from the port into the interior of the vessel for fanning out and decreasing the velocity of the incoming flow before and as it enters the interior of the vessel.

4. Apparatus according to claim 3, wherein the flow distributing structure also comprises a baffle against which the flow from the port is directed for diverting the flow into and through the expansion chamber for entry into the interior of the vessel.

5. Apparatus according to claim 4, wherein the separation vessel comprises a cylindrical body of ring formation and flat top and bottom walls closing said body, the ports passing through said top and bottom walls, respectively, at diametrically opposite locations which are uppermost and lowermost, respectively, when the vessel is in tilted position, at least the lower port opening into the corresponding end face of said body, which serves as the baffle, and the expansion chamber of the flow distributing structure being formed in the inside face of the said bottom wall at its juncture with the cylindrical body.

6. Apparatus according to claim 5, wherein the lower port is directed against the baffle at an angle of substantially ninety degrees.

7. Apparatus according to claim 6, wherein the expansion chamber is circular and has about one-half of its area disposed in the junction between the cylindrical body and the bottom wall.

8. Apparatus according to claim 1, wherein the separation vessel comprises a cylindrical body of ring formation and flat top and bottom walls closing said body, the ports passing through said top and bottom walls, respectively, at diametrically opposite locations which are uppermost and lowermost, respectively, when the vessel is in tilted position.

9. Apparatus according to claim 8, additionally comprising mounting means for the separation vessel, said mounting means comprising a platform adapted to receive the separation vessel in horizontal position, and means for moving said platform between horizontal and tilted positions and vice versa, said moving means being adapted to accelerate movement of the platform to about the midpoint of said movement and to decelerate said movement beyond said midpoint.

10. Apparatus according to claim 9, wherein the moving means comprises one-half sinusoidal electric motor means arranged to move the platform to the tilted position and back to the horizontal.

11. Apparatus according to claim 8, wherein the top and bottom walls are removably attached to the cylindrical body; and wherein sealing means are interposed between said body and said walls.

12. Apparatus according to claim 11, wherein the sealing means are respective O-rings set into receiving grooves formed around the outer margin of the end faces, respectively, of the cylindrical body.

13. Apparatus for separating cells of differing sedimentation velocities, comprising a closed separation vessel having an open and unobstructed interior; a relatively very small lower port located at the lowermost level of the interior of said vessel, the opening into the interior of the vessel of at least the lower port being offset from the interior of said vessel; and flow distributing means associated with at least said lower port and having flow distributing structure located between the port and the interior of the vessel and offset from the interior of the vessel for fanning out and decreasing the velocity of the incoming flow, thereby reducing the tendency of the incoming liquid to disturb isodense layers of liquid contained in the vessel.

14. Apparatus according to claim 13, wherein the flow distributing means also comprises flow distributing structure located between the upper port and the interior of the vessel.

15. Apparatus according to claim 1, wherein the flow distributing means means comprises flow distributing structure located between the upper port and the interior of the vessel.

16. A method for separating cells of differing sedimentation velocities, comprising the steps of tilting from horizontal position a separation vessel constructed in accordance with claim 1; introducing a density gradient liquid through the lower port and distributing its flow by means of a baffle or expansion chamber or both before and as it enters the interior of the vessel; filling the vessel with said gradient liquid until flow out of the upper port begins; loading the vessel with a cell suspension containing cells which are to be separated according to differences in sedimentation velocity, said loading being by way of the flow distributing means so said cell suspension will be distributed before and as it enters the interior of the vessel; moving the vessel back to horizontal position so that the isodense layers of the gradient liquid decrease in thickness with respect to their thickness when the vessel is in the tilted position; leaving the vessel in the horizontal position for a sufficient period of time to allow the cells in the cell suspension to separate on the gradient according to their respective sedimentation velocities; again tilting the separation vessel so as to increase the thickness of the isodense layers; and collecting the isodense layers of gradient liquid as various fractions, by removing the gradient liquid through the lower port.

* * * * *